US012708479B2

(12) United States Patent
Kowarschik et al.

(10) Patent No.: US 12,708,479 B2
(45) Date of Patent: Aug. 18, 2026

(54) METHOD AND DEVICE FOR MONITORING AN INTERVENTIONAL PROCEDURE

(71) Applicant: Siemens Healthcare GmbH, Erlangen (DE)

(72) Inventors: Markus Kowarschik, Nuremberg (DE); Markus-Hermann Koch, Forchheim (DE); Marcus Pfister, Bubenreuth (DE)

(73) Assignee: Siemens Healthineers AG, Forchheim (DE)

(*) Notice: Subject to any disclaimer, the term of this patent is extended or adjusted under 35 U.S.C. 154(b) by 403 days.

(21) Appl. No.: 18/227,931

(22) Filed: Jul. 29, 2023

(65) Prior Publication Data

US 2024/0033036 A1 Feb. 1, 2024

(30) Foreign Application Priority Data

Jul. 29, 2022 (DE) ..................... 10 2022 207 877.2

(51) Int. Cl.

*A61B 90/00* (2016.01)
*A61B 34/00* (2016.01)
*A61B 34/30* (2016.01)
*A61M 25/01* (2006.01)

(52) U.S. Cl.

CPC .............. *A61B 90/37* (2016.02); *A61B 34/30* (2016.02); *A61B 34/76* (2016.02); *A61M 25/0113* (2013.01); *A61B 2034/301* (2016.02); *A61B 2090/376* (2016.02)

(58) Field of Classification Search

None

See application file for complete search history.

(56) References Cited

U.S. PATENT DOCUMENTS

2004/0106916 A1* 6/2004 Quaid .................... A61B 34/71 606/1
2010/0076309 A1 3/2010 Wenderow et al.
2012/0179167 A1 7/2012 Wenderow et al.
2015/0126862 A1 5/2015 Pfister
2019/0021797 A1* 1/2019 Dyer ...................... A61B 34/20

(Continued)

FOREIGN PATENT DOCUMENTS

CN 113766868 A * 12/2021 ........ A61M 25/0116
DE 102013222674 B3 10/2014

(Continued)

OTHER PUBLICATIONS

CN113766868A translation (Year: 2021).*

(Continued)

*Primary Examiner* — Lina Cordero
(74) *Attorney, Agent, or Firm* — Lempia Summerfield Katz LLC

(57) ABSTRACT

To enhance safety of interventional procedures, a method for monitoring an interventional procedure that is carried out using an artificial object, such as a catheter, is provided. At least one image of the interventional procedure is acquired. The at least one image is analyzed automatically with regard to a specified anomalous feature relating to a geometry and/or a time-dependent movement parameter and/or a flow behavior of the artificial object. A complication signal is automatically generated only if the specified anomalous feature is detected in the at least one image.

20 Claims, 1 Drawing Sheet

(56) References Cited

U.S. PATENT DOCUMENTS

| | | | | |
|---|---|---|---|---|
| 2020/0005472 | A1* | 1/2020 | Terunuma | A61N 5/1049 |
| 2020/0129740 | A1 | 4/2020 | Kottenstette et al. | |
| 2020/0246088 | A1* | 8/2020 | Mewes | A61B 6/12 |
| 2020/0337782 | A1* | 10/2020 | Glassman | A61B 34/32 |
| 2021/0338346 | A1 | 11/2021 | Kaethner et al. | |
| 2024/0221152 | A1* | 7/2024 | Kono | A61B 6/465 |

FOREIGN PATENT DOCUMENTS

| | | | |
|---|---|---|---|
| DE | 102020205546 | A1 | 11/2021 |
| EP | 3406291 | B1 | 12/2019 |

OTHER PUBLICATIONS

Eng, Marvin H., et al. "Enhanced stent visualization: a case series demonstrating practical applications during PCI." International Journal of Cardiology 141.1 (2010): e8-e16.

Harris, Robert J., et al. "Classification of aortic dissection and rupture on post-contrast CT images using a convolutional neural network." Journal of Digital Imaging 32.6 (2019): 939-946.

* cited by examiner

METHOD AND DEVICE FOR MONITORING AN INTERVENTIONAL PROCEDURE

This application claims the benefit of German Patent Application No. DE 10 2022 207 877.2, filed on Jul. 29, 2022, which is hereby incorporated by reference in its entirety.

BACKGROUND

The present embodiments relate to a method for monitoring an interventional procedure. The present embodiments further relate to a corresponding device for monitoring such an interventional procedure.

Doctors in training benefit from having an experienced doctor monitoring, for example, an endovascular intervention using an X-ray angiography system, where the experienced doctor follows the course of the intervention in a monitoring or control room with the aid of live images and, if necessary, gives feedback. Such live images are typically fluoroscopy images, digital subtraction angiography (DSA) images, or optionally also intraprocedural 3D images. However, in larger centers, there are usually only very few experienced doctors available for monitoring purposes, while the number of trainee doctors is relatively high. Simultaneously, monitoring several trainee doctors is barely possible even for an experienced doctor.

In the case of remote-controlled procedures, a doctor operates, for example, a telemanipulator or a robotic system from a distance, for example, to carry out an interventional procedure. Here too, it is necessary to transmit live images to the doctor carrying out the procedure. In this situation, the problem arises of a lack of tactile feedback. For example, the doctor carrying out the procedure cannot feel whether the catheter to be inserted is coming up against resistance. This leads to a risk of injury to vessels.

Document DE 10 2020 205 546 A1 discloses a monitoring method and a medical system for improved patient safety. The method serves to automatically monitor a robot-assisted movement, performed by a robotic system, of a medical object through a cavity in a body of the patient. The movement of the medical object is tracked using a medical imaging device such that the medical object and/or the hollow organ is/are arranged at least in part in the capture region mappable by the imaging device. In each case current image and/or sensor data from a sensor associated with the robotic system or the object is evaluated as to whether a decision and/or safety-relevant situation prevails for the robotic system.

SUMMARY AND DESCRIPTION

The scope of the present invention is defined solely by the appended claims and is not affected to any degree by the statements within this summary.

The present embodiments may obviate one or more of the drawbacks or limitations in the related art. For example, monitoring of interventional procedures is improved.

According to the present embodiments, a method for monitoring an interventional procedure that is carried out using an artificial object is provided. In the interventional procedure, the artificial object is introduced, for example, into the body of a patient. A catheter is inserted into a vessel in the body of the patient, for example. A biopsy needle may, however, also be guided into a tumor in a body of the patient. The artificial object may, however, also be guide wires, stents, and the like. A contrast agent is, for example, also regarded as an artificial object, however. It is precisely this interventional procedure, in which the artificial object is used, that is to be monitored using the method according to the present embodiments. The monitoring is necessary, for example, to increase patient safety.

The method according to the present embodiments involves the acquisition of at least one image of the interventional procedure. As a rule, a stream of images (e.g., low-dose X-ray images) is obtained, so as to enable real-time tracking of the interventional procedure. The image or images may be acquired using any image-generating device. For example, magnetic resonance imaging (MRI) images, computed tomography (CT) images, or ultrasound images may be obtained.

In a further act, the at least one image is automatically analyzed with regard to a specified anomalous feature relating to a geometry and/or a time-dependent movement parameter and/or a flow behavior of the artificial object. The image or the corresponding sequence of images is thus automatically analyzed, which may proceed, for example, using appropriate image processing. The image or images is/are analyzed with regard to a specific geometry of the artificial object, for example. If, for example, the artificial object is a catheter, a portion of the catheter tube may assume a particular shape or geometry during the interventional procedure. For example, the artificial object may remain straight, become wavy, or even form a loop. If, for example, waviness is defined as the specified anomalous feature, every image may be analyzed for this waviness or the anomalous feature. The same is true of other anomalous features, such as, for example, a time-dependent movement parameter. Such time-dependent movement parameters may, for example, be the speed or acceleration that a catheter tip exhibits or undergoes during the interventional procedure. Optionally, this time-dependent movement parameter is defined as an anomalous feature only if a specified threshold value is exceeded (e.g., if the speed or the acceleration is above a specific threshold value). Alternatively or in addition, the flow behavior of the artificial object may also constitute an anomalous feature. If, for example, contrast agent flows into unintended areas of the body of the patient, such an anomalous feature may be present. In this case, the artificial object is thus flowing into undesired spatial areas, providing there is a high probability that an anomaly or a risk is present.

In a further act of the method according to the present embodiments, a complication signal is automatically generated only if the specified anomalous feature is detected in the at least one image. The complication signal may, for example, be the light signal from a red lamp, an acoustic warning signal, or an instruction to act. The complication signal may, however, also take the form of a precursor of these signals, which results from the automatic analysis of the image with regard to the specified anomalous feature. This complication signal is thus generated precisely and only when this anomalous feature has been ascertained in the image or in the images. Otherwise, if the anomalous feature is not ascertained, the complication signal is not generated. An underlying raw signal may, for example, be a binary one. The binary one is not generated if no anomaly is present. With the assistance of the complication signal, additional information about the interventional procedure is thus provided. This additional information may be used to monitor the interventional procedure.

In a development of the method according to the present embodiments, provision is made for the anomalous feature to relate to a curvature, a loop structure, or a waviness of the artificial object, and for the anomalous feature to be detected only if the geometry of the artificial object deviates from reference data with regard to a specified object geometry. As has already been indicated above, the artificial object may be an instrument, a guide wire, a tube, or the like, with, for example, flexible properties. During the interventional procedure, such an instrument may, for example, become curved. Further, this instrument (e.g., a catheter) may become wavy if the instrument meets with resistance at the distal end but continues to be pushed in at the proximal end.

In other cases, a catheter, guide wire, or the like may also assume a loop structure if it is correspondingly deflected in a cavity. All these specific deformations of the artificial object during the interventional procedure may cause complications. Provision is made, for example, for the catheter to have a straight profile in a specific area during the interventional procedure. Such a straight profile may be defined by reference data. If the actual object geometry deviates from the specified (e.g., straight) object geometry, a corresponding anomaly is present, and the corresponding anomalous feature is detected. A deviation may be identified by the deviation exceeding a specified amount. The deviation may optionally also be identified by the actual object geometry falling into a different category than the specified object geometry. Thus, for example, one category covers straight profiles of the artificial object, and another category covers round or looped profiles of the artificial object.

In an alternative development of the method according to the present embodiments, provision is made for the anomalous feature to relate to a speed or acceleration or jerking of the artificial object, and for the anomalous feature to be detected only if the speed or acceleration or jerking deviates from specified reference data. For example, the speed, the acceleration, or the jerking relates to a part of the artificial object (e.g., the tip of a catheter). If, for example, the shape of the distal end of a catheter changes abruptly, a corresponding speed or acceleration or jerking of the tip of the catheter may be identified. These identified parameters may deviate from specified reference data with regard to these variables. If, for example, the speed of the catheter tip thus deviates by a specified amount from a specified speed, this constitutes an anomaly. The same applies to the other parameters.

In a further embodiment, provision is made for the anomalous feature to relate to a speed (e.g., current speed) of a tip of an instrument (e.g., catheter or the like) with which the interventional procedure is being carried out, and for the anomalous feature to be detected only if a movement of the tip of the instrument used in the interventional procedure does not correlate as specified with reference data relating to a robotic movement for guiding the instrument. The instrument is, for example, thus guided into a vessel by a robot, for example. The insertion speed has a specific value. If the tip of the inserted instrument has a different speed value, an anomaly may be present. If, for example, the tip of the catheter moves more quickly than the insertion speed, this may indicate slackening of the catheter, as may occur in the event of dissection of a vessel in a body of the patient or piercing of a vessel wall. If the speed of the catheter tip is lower than the insertion speed or the movement of the robot, this may indicate that the tip has got stuck. Further feeding of the instrument may result in corresponding complications.

In a further embodiment, the anomalous feature relates to incomplete deployment of an instrument in a patient in whom the interventional procedure is being carried out, and the anomalous feature is detected only if a shape (e.g., current shape) of the instrument deviates from specified reference data. If the instrument is a stent or balloon, for example, it is important for this instrument to be deployed correctly at the intended location. Otherwise, if deployment is incomplete, complications may ensue. For monitoring, it is thus to be established whether the instrument has been deployed as desired and is thus assuming a specific shape or geometry. The specific shape is defined by the specified reference data. Deviation therefrom thus leads to the conclusion that deployment of the instrument is incomplete.

In a further embodiment, provision is made for the anomalous feature to relate to contrast medium flow, and for the anomalous feature to be detected only if a pattern of contrast medium flow deviates from specified reference data. A current contrast medium flow may thus, for example, have the shape of a previously identified vessel tree. If, however, a rupture, dissection, distal embolism, or the like is present, unintended flow arises or flow is stopped in a region of the body of the patient in which the interventional procedure is being carried out. In such cases too, it is advantageous if a corresponding complication signal is provided in the context of automatic monitoring.

The above-described embodiments may also be combined. Thus, for example, all the anomalous features that have been outlined above may be monitored in parallel. For example, the images may be analyzed with regard to both curvatures, waviness, and loops and additionally to a speed, acceleration, or jerking, and optionally also to a desired deployment. Further anomalous features or selected ones thereof may also be taken into account in the analysis.

In a further development, provision may be made for a plausibility check to be carried out, and for the complication signal to be generated only if the analysis data from the automatic analysis of the at least one image matches corresponding data from a data source other than the image source. Thus, the image or the images relating to the anomalous feature (e.g., optionally a plurality of anomalous features) is/are analyzed, and a plausibility check is additionally undertaken to increase certainty that the complication signal is not being output erroneously. The plausibility check involves evaluating additional data that originates from a data source other than the image source. Such a data source may, for example, be a log data source that makes "live logs" available. The data source may include one or more specific sensors, such as, for example, a camera. The data (e.g., dimensions) obtained from the images may be compared or matched with the data from these other sensors.

In one embodiment, the artificial object may be automatically detected in the at least one image. This provides that, for example, a catheter is identified automatically as such in the image analysis. Thus, for example, not only the geometry of the artificial object but also its identity or type is automatically identified. This has the advantage, for example, that reference data may be obtained automatically, for example, from a database of reference data about the type of artificial object. The data is used to detect the respective anomalous feature. Thus, for example, not only the type of artificial object but also any anomaly of the artificial object that may be present may be automatically ascertained.

The method according to the present embodiments may be advantageously used in special situations. Thus, for example, provision is made in one embodiment for the interventional procedure to take place in a treatment room of a building and for the at least one image and the complication signal to be transmitted into a monitoring room other than the treatment room. This opens up the possibility of being able to carry out monitoring in a room other than the treatment room (e.g., operating room). Instead, monitoring may also proceed in a room that has to meet lower sterility requirements. Thus, for example, an experienced doctor may monitor an operating trainee doctor from an adjoining room or even over greater distances.

According to a further embodiment, the interventional procedure in a treatment room is remote-controlled by a person in the monitoring room. This is advantageous, for example, if relatively long distances are bridged in this way. For example, just one experienced doctor may be available to multiple hospitals over a relatively large area. In this case, it may be advantageous if the specialist may undertake the respective interventional procedures via remote control, receiving corresponding complication signals in the course of automatic monitoring. These complication signals may therefore also be of particular significance, since the doctor working by remote control does not receive any tactile feedback when, for example, the doctor inserts a catheter into a patient. Increasing resistance during insertion may be ascertained via corresponding speed signals and made available to the doctor in the form of a complication signal.

In a further embodiment, in addition to the one interventional procedure, at least one further interventional procedure may take place in a further treatment room, from which in each case likewise at least one image and accordingly a respective complication signal is transmitted into the monitoring room. If, namely, an experienced specialist is to monitor multiple treatments simultaneously, for example, the experienced specialist may rapidly reach the limit of their capacity. If, however, such a specialist is supported in their monitoring of multiple treatments by corresponding complication signals, greater monitoring safety may be provided.

The above-stated methods generally use reference data to identify an anomaly or detect a corresponding anomalous feature. Such reference data may be predetermined and automatically learned. This learning may proceed using artificial intelligence. For example, the reference data may represent a vessel tree, the shape of which was ascertained by artificial learning. Further, specific parameters of the artificial object may also be learned, such as, for example, waviness of a catheter in a vessel if the catheter tip comes up against resistance. Likewise, speed data as well as other parameters of the artificial object that may arise during the interventional procedure may be learned.

According to the present embodiments, a device for monitoring an interventional procedure is also provided. The device includes an acquisition device for acquiring at least one image of the interventional procedure. The device also includes an analysis device for automatically analyzing the at least one image with regard to a specified anomalous feature relating to a geometry and/or a time-dependent movement parameter and/or a flow behavior of the artificial object. The device also includes a signal generation device for automatically generating a complication signal only if the specified anomalous feature is detected in the at least one image.

The advantages and further developments outlined above in relation to the method according to the present embodiments apply mutatis mutandis also to the device according to the present embodiments. In this case, the corresponding method features may be regarded as functional features of the device.

In addition, provision may be made for an anomaly that relates to a current geometry of a vessel in the body of a patient on whom the interventional procedure is being carried out to be monitored. A corresponding anomalous feature is optionally detected only if the geometry of the vessel during the interventional procedure deviates from pre-interventional reference data. Thus, for example, the starting point may be a specified vessel geometry, which may change due to insertion of the artificial object. If this change exceeds a specified amount, this may provide an anomaly that leads to complications. This anomaly may optionally also be identified by the current shape of a catheter deviating from the original vessel shape prior to the intervention.

Deviation of the current instrument shape from the original vessel geometry may also indicate that the vessel is currently perforated. In this case, a corresponding anomalous feature may likewise be identified, or a corresponding complication signal may be generated.

A further anomalous feature may relate to the movement of a patient on whom the interventional procedure is being carried out. This anomalous feature may only be detected if a movement of one or more landmarks in or on the patient corresponds to specified reference data. This may be the case if the patient makes a specified movement pattern. If, for example, the patient makes rapid, sweeping movements, this indicates patient stress, which may likewise lead to complications.

An anomaly may arise if the artificial object is, for example, free to move in a patient and migrates into an undesired region of the patient. In this case, the anomalous feature may only be detected if the position of the object deviates from specified reference data (e.g., from a predetermined position). In this way, for example, distal embolisms or unintended inflows may be identified during monitoring.

In general, the above-outlined monitoring may be carried out by a person, but the monitoring may also be performed by automated devices. In the simplest case, monitoring amounts to nothing more than generation of the complication signal. The complication signal may, however, also be further processed by automated methods.

A method described herein may also take the form of a computer program or computer program product that the method implements on the device, or a corresponding control unit when the method is executed thereon. An electronically readable data storage medium with electronically readable control information stored thereon may likewise be present. The control information includes at least the described computer program. The control information may be configured such that, when the data storage medium is used in a control unit of an MR system, the control information carries out the described method.

For application cases or application situations that may arise during the method and are not described explicitly here, provision may be made for an error message and/or a request to submit user feedback to be output and/or a default setting and/or a predetermined initial state to be set.

DETAILED DESCRIPTION

Figure 1:
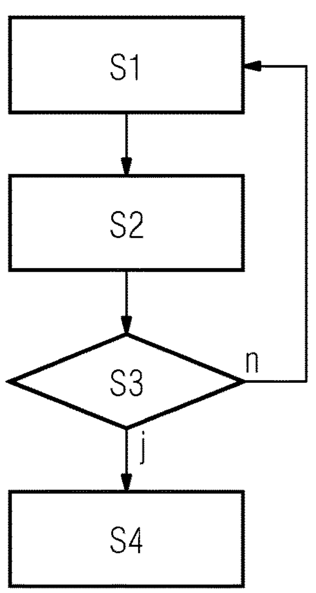
FIG. 1 shows a schematic flowchart for an embodiment of a method.

The schematic block diagram of FIG. 1 reproduces the method acts that may be provided in an embodiment of a monitoring method of an interventional procedure. In act S1, one or more images may be acquired by an imaging device, such as, for example, a CT device, to enable monitoring of the interventional procedure. Other imaging devices such as MR devices, ultrasound devices, and the like may be used for this purpose. In order to enable instantaneous monitoring of the interventional procedure, the images may be obtained in real time.

In act S2, the image or images is/are automatically analyzed with regard to a specified anomalous feature. This anomalous feature relates to a geometry and/or a time-dependent movement parameter and/or a flow behavior of the artificial object. The image or images is/are thus evaluated with regard to one or more of the stated parameters. In this way, an anomalous shape or geometry, an anomalous movement, and/or an anomalous flow of the artificial object (e.g., catheter, contrast agent, or the like) may be investigated. Multiple analyses with regard to different anomalous features are optionally carried out in parallel.

In a further act S3, a decision is taken as to whether one or more anomalous features have been detected. If no anomalous feature is detected, the method may resume at act S1. If an anomaly is discovered, the next act S4 is carried out. In this act, a complication signal is generated, with which the information may be provided that an anomaly is present and under certain circumstances complications are imminent or have arisen.

The images acquired in act S1 and the complication signal generated in act S4 are optionally transmitted to another room than the acquisition room and presented to an operator. In this way, for example, a doctor may monitor the interventional procedure in an adjoining room.

Figure 2:
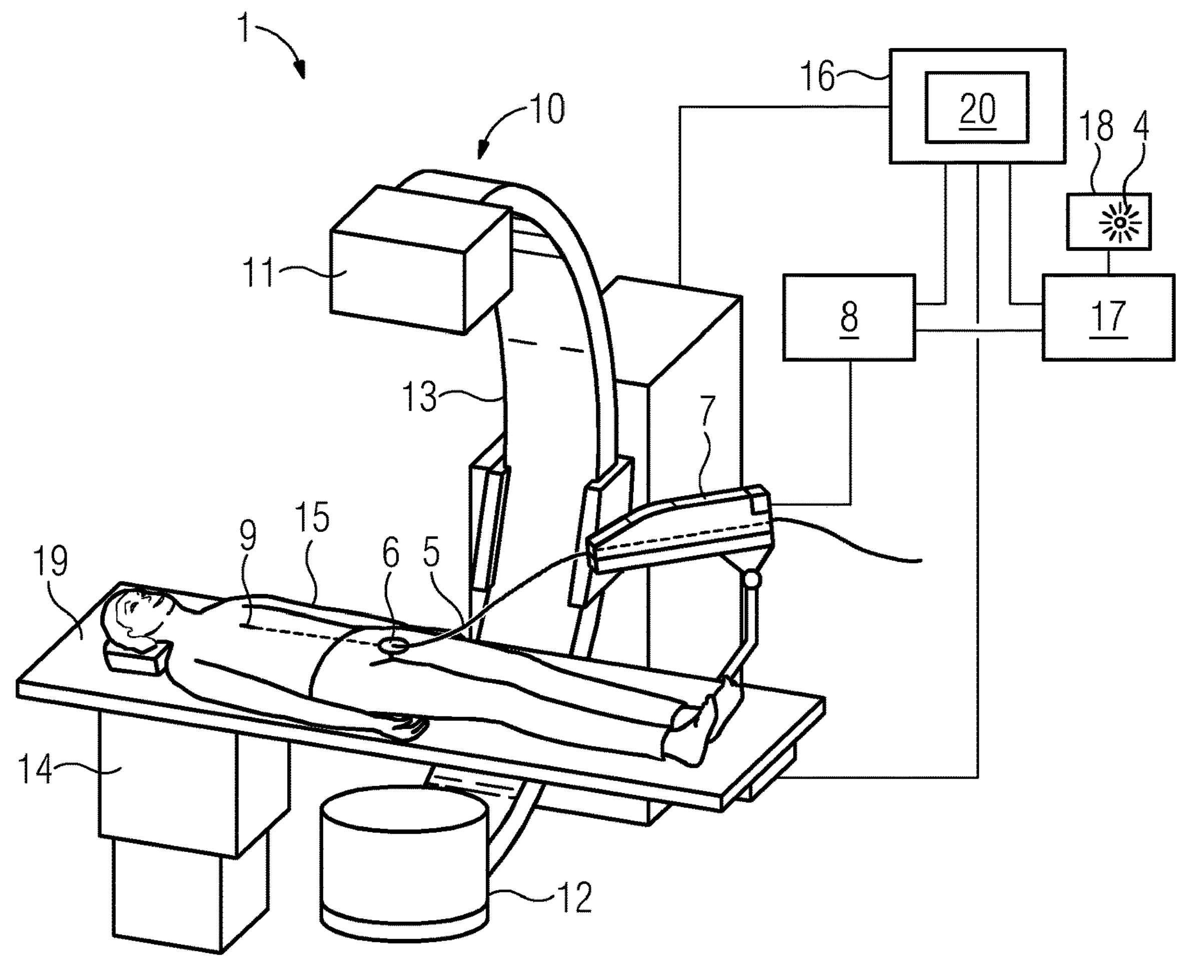
FIG. 2 shows a schematic representation of an embodiment of a device for monitoring an interventional procedure.

FIG. 2 shows a medical system 1 that is configured to carry out the method.

The medical system 1 optionally has a robotic system and an imaging device (e.g., an X-ray machine 10). The robotic system is optionally configured for semi-automatic or automatic feed of at least one object (e.g., an instrument, stent, guide wire 5, or catheter) into a hollow organ in the body of a patient 15. Semi-automatic actuation may be, for example, actuation transmittable by an operator via an input unit 17 (e.g., joystick, touchpad, rotary knob, etc.) to a robot control unit 8. The robotic system thus has, for example, the robot control unit 8 and a robot-assisted drive system 7. The drive system 7 is configured to move the medical object (e.g., a guide wire 5) based on control signals from the robot control unit 8 after insertion at an entry point 6 into a hollow organ in the body of a patient 15. The drive system 7 includes, for example, at least one drive and a drive mechanism (not shown, for example, known from EP 3406291 B1). The drive mechanism is detachably coupled, for example, to the guide wire 5. The guide wire 5 may be advanced and retracted axially and/or additionally moved rotationally using the drive mechanism and the drive. The robot control unit 8 is connected to the input unit 17 (e.g., arranged at a distance (remotely) from the patient) that an operator (e.g., a surgeon) may operate. The control signals are transmitted from the input unit 17 (e.g., one or more joysticks, touchpads, control knobs, etc.) to the robot control unit 8, and in this way, movement of the object is actuated semi-automatically. Alternatively, the operator may also undertake path planning for the object or cause this to be drawn up automatically. This is transmitted to the robot control unit 8, thus enabling fully automatic movement. Path planning may also be used as a reference for semi-automatic movement.

The imaging device (e.g., the X-ray machine 10) is provided to gain an overview of the intervention and movement. The X-ray machine 10 has a C-arm 13, for example, that supports an X-ray source 12 and an X-ray detector 11 and is connected to a system controller 16. The C-arm 13 is arranged so as to be movable relative to the patient 15. In the case of a mobile X-ray machine, the entire X-ray machine may also be displaced. Alternatively or in addition, the patient table 14 or just the surface 19 of the patient table 14 may also be moved relative to the X-ray machine or image-capture system. Using the X-ray machine 10, images of a mappable capture region may be prepared and displayed on a display unit 18. The robot control unit 8 and the system controller 16 of the imaging device may exchange data bidirectionally and communicate with one another. The system controller 16 may be equipped with a processor 20 that assumes the tasks of control and optionally image processing and analysis. A common controller may also be provided, which includes the robot control unit 8 and the system controller 16.

The above-mentioned act S1 of acquiring one or more images is performed, for example, by the X-ray machine 10. The further acts S2 to S3 relating to analysis of the images, identification of an anomaly, and generation of a complication signal may be performed by the system controller. The display unit 18 and optionally also a part of the system controller 16 may be arranged in a different room from the treatment room. A separate display unit may also be provided in the monitoring room (not shown).

The system illustrated enables automation of monitoring of interventional procedures based on the image information and automated indication of complications, the risk of complications, or unusual situations. For example, in the case of remote-controlled procedures using a robotic system, such approaches are of particular significance, since workflow efficiency and patient safety may potentially be enhanced. In such cases, not only image information but also data from the robotic system may be used to indicate complications, the risk of complications, or unusual situations.

The underlying concept consists in the analysis of X-ray images, for example, and the identification of deviations from "normal" behavior (e.g., of guide wires or contrast agent flow), which may indicate complications. To this end, for example, structures and effects are automatically detected in "live" images. To this end, the instruments in use may be detected beforehand in the "live" images. This may be achieved, for example, using conventional image processing or using learning-based approaches. A corresponding optical or acoustic complication signal may optionally be output in a corresponding output device such as the display unit 18.

In principle, identification and assessment (e.g., measurement) of curvatures of the instrument (e.g., in general terms: artificial object) detectable in the image (e.g., "live" image) is thus possible using, for example, learning-based (e.g., data-driven) approaches (AI) or using conventional image processing methods. Further, identification of loops in the guide wire or the like is also possible using learning-based approaches or also using conventional image processing methods (e.g., using a Hough transformation).

Further, abnormal contrast agent flows may also be identified based on automated monitoring using learning-based approaches (e.g., through comparisons with expected contrast agent flow patterns) or using conventional approaches (e.g., comparison of a "live" image with contrast agent with an image from a previously acquired digital subtraction angiography series). Further, evaluation of the deviation of detected instruments from the original shape of the respective vessel (e.g., extractable from a pre-interventional 3D image or a DSA data set acquired beforehand) may also be possible. Here, the use of pre-interventional 3D images presupposes registration thereof with the coordinate system of the angiography system.

A number of examples are listed below for which the present embodiments may be used. Some examples relate to the administration of contrast agent, while other examples do not require any contrast agent administration.

Examples not requiring administration of contrast agent are provided below. For example, an instrument may be too hard. An instrument, such as, for example, a guide wire or catheter is too hard or too rigid. A clear deviation of the shape of the instrument from the original shape of the respective vessel may be identified. The original shape of a vessel may, for example, be extracted from a pre-interventional 3D image or a DSA data set acquired beforehand.

As another example, an instrument may be too soft. For example, an instrument is too soft or too elastic. An instrument that is too soft may be identified if the shape of the instrument is too wavy (e.g., integral over the curvature along the detected instrument in the vessel is above a predefined threshold value) or even has loops. Further, in the case of an interventional procedure performed by robot, increasing waviness of the instrument may be identified in that the distance covered per unit of time by the tip 9 of the instrument deviates markedly from the corresponding robotic instrument feed.

As another example, an instrument may be off the planned path. For example, an instrument is not or no longer on a planned path. A "guidance map" or the like is needed, for example, for the intervention in order to have the planned path as reference. Using this, it may be established whether the position of the instrument deviates too far (e.g., threshold value optionally necessary) from the planned path in the vessel tree.

As another example, perforation of vessel wall is identified. Perforation of the vessel wall may, for example, be identified because the geometric shape of the instrument detectable in the "live" image deviates significantly from the original shape of the respective vessel, such that deformation of the vessel may be ruled out. Perforations may possibly also be identified by the shape of the instrument changing abruptly (e.g., slackening) at least at the distal end thereof. This requires the shape of the instrument in the vessel tree to be evaluated continuously in each case via multiple "live" images.

As another example, potential dissection of a vessel may be identified. A dissection may be identified, for example, because the instrument has "got stuck". In other words, movement of the instrument by the robot does not result in any movement at the tip of the instrument. This may be automatically identified by rotation about the instrument axis (e.g., 90 degrees) being performed by robot.

As another example, patient stress may be identified. Complications may also be identified based on spontaneous patient movements or changes in heart/respiratory rate. Such complications have conventionally otherwise been identified by an on-site anesthetist based on vital parameters. In the image, this may be detected during automatic monitoring by an analysis of the movement of dedicated landmarks or time-dependent displacement vector fields, which characterize the location-dependent, not necessarily periodic movements in the "live" images.

As another example, an instrument has been let go, or material has migrated into undesired areas. An instrument that has been let go or material, such as, for example, a stent, a balloon, an embolizate, etc., may be detected in an incorrect or undesired region if a "guidance map" is available or the path/planned position is obvious. This requires identification of the instrument or material in successive images and analysis of the position thereof.

As another example, an instrument may be incompletely deployed. Incomplete deployment of an instrument such as, for example, a stent or balloon may be identified, for example, by comparing the current shape of the instrument with a geometric model thereof. This model does not necessarily have to be highly accurate. A stent may, for example, be approximated as a curved cylindrical shape (e.g., radius largely constant along the length thereof). If the shape detected in the image deviates significantly (e.g., threshold value optionally necessary) therefrom, this may point toward a complication.

As another example, an internal instrument malfunction may be identified. Malfunction of the instrument or of the drive or controller of the instrument may be identified, for example, based on the images and further data. Robot log-in data may be used, for example. Plausibility checks may be carried out by cross-comparisons of log-in data with "live" images. In this way, it may, for example, be checked whether dimensions that are obtained from a first source match dimensions obtained from a second source with sufficient accuracy.

The remaining examples relate to interventional procedures with contrast agent administration.

As another example, rupture/dissection may be detected. A rupture or dissection may be detected, for example, by abnormal contrast agent flows. For example, contrast agent is exiting from a vessel, or contrast agent is stagnating in a vessel portion. Identification of such an occurrence requires comparison and analysis of multiple images.

As another example, distal embolism or unintended inflow into regions to be protected may be detected. A complication with regard to embolization (e.g., intentional occlusion) may be detected, for example, by comparing intra-operative and pre-interventional images (e.g., DSA images) or using learning-based approaches, which may identify "cut-off" vessel branches.

Needle-based procedures, such as, for example, the ablation of tumors in the liver or kidney or other puncture procedures, may also benefit from the present embodiments.

In the examples outlined above, the approach proposed in each case allows interventional procedures to be automated, which has the potential to lead to more efficient workflows that are safer for the patient and result in correspondingly improved treatment quality. This is particularly significant if the procedure is remote-controlled using a robot. In such a case, the experienced user may potentially be a long distance away from the patient and from the local treating doctor, such that automated approaches are particularly significant in terms of increasing patient safety and maintaining high treatment quality.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for monitoring an interventional procedure that is carried out using an artificial object, the method comprising:

acquiring, by an acquisition device, at least one image of the interventional procedure;

automatically analyzing the at least one image with regard to a specified anomalous feature relating to a geometry, a time-dependent movement parameter, a flow behavior, or any combination thereof of the artificial object;

automatically generating a complication signal only when the specified anomalous feature is detected in the at least one image; and carrying out a plausibility check, wherein the complication signal is automatically generated only when analysis data from the automatically analyzing of the at least one image matches corresponding data from a data source other than a source of the at least one image, and wherein the data source comprises a log data source that makes live logs available, one or more sensors, or any combination thereof.

2. The method of claim 1, wherein the specified anomalous feature relates to a curvature, a loop structure, or a waviness of the artificial object, and the specified anomalous feature is detected only when the geometry of the artificial object deviates from reference data with regard to a specified object geometry.

3. The method of claim 2, wherein the reference data is obtained by artificial learning.

4. The method of claim 1, wherein the specified anomalous feature relates to a speed, an acceleration, or a jerking of the artificial object, and the specified anomalous feature is detected only when the speed, the acceleration, or the jerking deviates from specified reference data.

5. The method of claim 1, wherein the artificial object is an instrument, the specified anomalous feature relates to a speed of a tip of the instrument with which the interventional procedure is being carried out, and the specified anomalous feature is detected only when a movement of the tip of the instrument used in the interventional procedure does not correlate as specified with reference data relating to a robotic movement for guiding the instrument.

6. The method of claim 1, wherein the artificial object is an instrument, the specified anomalous feature relates to incomplete deployment of the instrument in a patient in whom the interventional procedure is being carried out, and the specified anomalous feature is detected only when a shape of the instrument deviates from specified reference data.

7. The method of claim 1, wherein the artificial object is a contrast agent, the specified anomalous feature relates to contrast medium flow, and the specified anomalous feature is detected only when a pattern of the contrast medium flow deviates from specified reference data.

8. The method of claim 1, wherein the artificial object is automatically detected in the at least one image.

9. The method of claim 1, wherein the interventional procedure takes place in a treatment room of a building, and wherein the method further comprises transmitting the at least one image and the complication signal into a monitoring room other than the treatment room.

10. The method of claim 9, wherein the interventional procedure in the treatment room is remote-controlled by a person in the monitoring room.

11. The method of claim 9, wherein at least one further interventional procedure takes place in a further treatment room, and wherein the method further comprises transmitting, from the further treatment room, in each case at least one image and a respective complication signal into the monitoring room.

12. The method of claim 1, wherein the one or more sensors includes a camera, a sensor associated with a robotic system, or the camera and the sensor associated with the robotic system.

13. A device for monitoring an interventional procedure, the device comprising:

an acquisition device configured to acquire at least one image of the interventional procedure;

an analysis device configured to automatically analyze the at least one image with regard to a specified anomalous feature relating to a geometry, a time-dependent movement parameter, a flow behavior, or any combination thereof of an artificial object; and a signal generator configured to;

automatically generate a complication signal only when the specified anomalous feature is detected in the at least one image; and carry out a plausibility check, wherein the complication signal is automatically generated only when analysis data from the automatic analysis of the at least one image matches corresponding data from a data source other than the acquisition device, and wherein the data source comprises a log data source that makes live logs available, one or more sensors, or any combination thereof.

14. The device of claim 13, wherein the one or more sensors includes a camera, a sensor associated with a robotic system, or the camera and the sensor associated with the robotic system.

15. A non-transitory computer-readable storage medium that stores instructions executable by one or more processors to monitor an interventional procedure that is carried out using an artificial object, the instructions comprising:

acquiring, by an acquisition device, at least one image of the interventional procedure;

automatically analyzing the at least one image with regard to a specified anomalous feature relating to a geometry, a time-dependent movement parameter, a flow behavior, or any combination thereof of the artificial object;

automatically generating a complication signal only when the specified anomalous feature is detected in the at least one image; and carrying out a plausibility check, wherein the complication signal is automatically generated only when analysis data from the automatically analyzing of the at least one image matches corresponding data from a data source other than a source of the at least one image, and wherein the data source comprises a log data source that makes live logs available, one or more sensors, or any combination thereof.

16. The non-transitory computer-readable storage medium of claim 15, wherein the specified anomalous feature relates to a curvature, a loop structure, or a waviness of the artificial object, and the specified anomalous feature is detected only when the geometry of the artificial object deviates from reference data with regard to a specified object geometry.

17. The non-transitory computer-readable storage medium of claim 15, wherein the specified anomalous feature relates to a speed, an acceleration, or a jerking of the artificial object, and the specified anomalous feature is detected only when the speed, the acceleration, or the jerking deviates from specified reference data.

18. The non-transitory computer-readable storage medium of claim 15, wherein the artificial object is an instrument, the specified anomalous feature relates to a speed of a tip of the instrument with which the interventional procedure is being carried out, and the specified anomalous feature is detected only when a movement of the tip of the instrument used in the interventional procedure does not correlate as specified with reference data relating to a robotic movement for guiding the instrument.

19. The non-transitory computer-readable storage medium of claim 15, wherein the artificial object is an instrument, the specified anomalous feature relates to incomplete deployment of the instrument in a patient in whom the interventional procedure is being carried out, and the specified anomalous feature is detected only when a shape of the instrument deviates from specified reference data.

20. The non-transitory computer-readable storage medium of claim 15, wherein the one or more sensors includes a camera, a sensor associated with a robotic system, or the camera and the sensor associated with the robotic system.

* * * * *